United States Patent
Magness

(10) Patent No.: US 10,080,680 B2
(45) Date of Patent: Sep. 25, 2018

(54) DENTAL APPLIANCE FOR TREATMENT OF BRUXISM

(71) Applicant: R. Joseph Magness, Orem, UT (US)

(72) Inventor: R. Joseph Magness, Orem, UT (US)

( * ) Notice: Subject to any disclaimer, the term of this patent is extended or adjusted under 35 U.S.C. 154(b) by 200 days.

(21) Appl. No.: 14/321,648

(22) Filed: Jul. 1, 2014

(65) Prior Publication Data

US 2015/0000677 A1    Jan. 1, 2015

Related U.S. Application Data

(60) Provisional application No. 61/841,682, filed on Jul. 1, 2013, provisional application No. 61/901,696, filed on Nov. 8, 2013.

(51) Int. Cl.
| | |
|---|---|
| *A61C 5/14* | (2006.01) |
| *A61F 5/56* | (2006.01) |
| A61C 7/08 | (2006.01) |
| A63B 71/08 | (2006.01) |

(52) U.S. Cl.
CPC ............ *A61F 5/566* (2013.01); *A61C 7/08* (2013.01); *A61F 5/56* (2013.01); *A63B 71/085* (2013.01)

(58) Field of Classification Search
CPC ...... A61F 5/56; A61F 5/566; A61F 2005/563; A61C 7/08; A61C 7/36; A61C 7/00; A63B 71/085; A63B 2071/088; A63B 2071/086; A63B 71/08; Y10S 602/902
See application file for complete search history.

(56) References Cited

U.S. PATENT DOCUMENTS

| | | | | |
|---|---|---|---|---|
| 5,427,117 A | * | 6/1995 | Thornton | ............... A61F 5/566 128/848 |
| 5,795,150 A | | 8/1998 | Boyd | |
| 5,823,193 A | * | 10/1998 | Singer | .................... A61F 5/566 128/848 |
| 5,868,138 A | * | 2/1999 | Halstrom | ............... A61F 5/566 128/848 |
| 6,581,603 B1 | | 6/2003 | Schames | |

(Continued)

OTHER PUBLICATIONS

Written Opinion of the International Searching Authority, International Application No. PCT/US2014/045162, dated Oct. 16, 2014, pp. 1-4.

(Continued)

*Primary Examiner* — Victoria J Hicks
(74) *Attorney, Agent, or Firm* — Warren M. Pate; Pate Peterson, PLLC

(57) ABSTRACT

A dental appliance for treating bruxism is disclosed. The appliance may include upper and lower portions. The upper portion may include a first base and a first feature. The first base may engage the upper teeth of a patient. The first feature may secure to an anterior area of the first base and include a concave surface forming a concavity. The lower portion may include a second base and a second feature. The second base may engage the lower teeth of the patient. The second feature may secure to an anterior area of the second base and include a protrusion. As the patient bites down, the protrusion may contact the concave surface at a point of contact that is a sole or initial contact between the upper and lower portions. Thus, the interaction of the protrusion and concave surface may control certain mandibular loadings and motions of the patient.

11 Claims, 16 Drawing Sheets

(56) References Cited

U.S. PATENT DOCUMENTS

| | | | |
|---|---|---|---|
| 6,666,212 | B2 | 12/2003 | Boyd, Sr. |
| 7,607,438 | B2 | 10/2009 | Pelerin |
| 7,654,267 | B2 | 2/2010 | Boyd |
| 8,156,940 | B2 | 4/2012 | Lee |
| 8,166,976 | B2 | 5/2012 | Webster et al. |
| 2004/0007239 | A1 | 1/2004 | Eubank |
| 2005/0072435 | A1 | 4/2005 | Eubank |
| 2006/0174897 | A1* | 8/2006 | Sarkisian ............. A61F 5/566 |
| | | | 128/859 |
| 2007/0125388 | A1 | 6/2007 | Thornton et al. |
| 2008/0199824 | A1 | 8/2008 | Hargadon |
| 2009/0308401 | A1* | 12/2009 | Orrico ................ A61F 5/566 |
| | | | 128/848 |
| 2011/0195376 | A1 | 8/2011 | Boyd, Sr. |
| 2014/0060549 | A1* | 3/2014 | Lucas ................. A61C 7/36 |
| | | | 128/861 |
| 2015/0007830 | A1* | 1/2015 | Remmers ............. A61F 5/566 |
| | | | 128/848 |

OTHER PUBLICATIONS

BruxSplint, www.chairsidesplint.com, pp. 1-8, accessed May 29, 2013.

Listing of NTI type and BruxSplint Devices, www.chairsidesplint.com, pp. 1-4, accessed May 29, 2013.

Night Guards, www.landmarkdental.net, pp. 1-2, accessed May 29, 2013.

\* cited by examiner

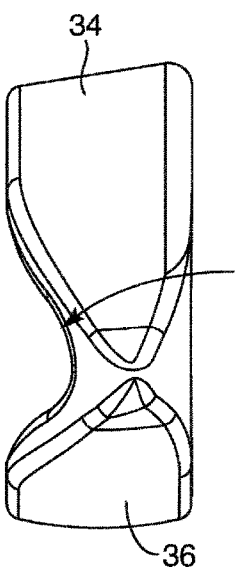
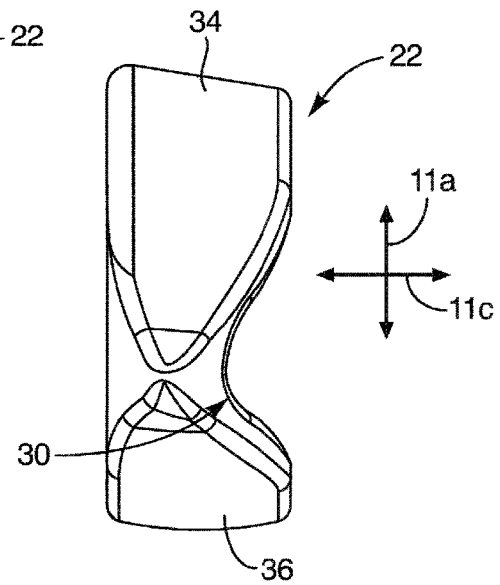
FIG. 8   FIG. 9
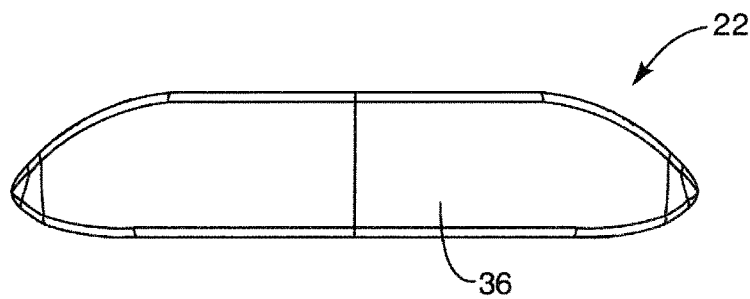
FIG. 10
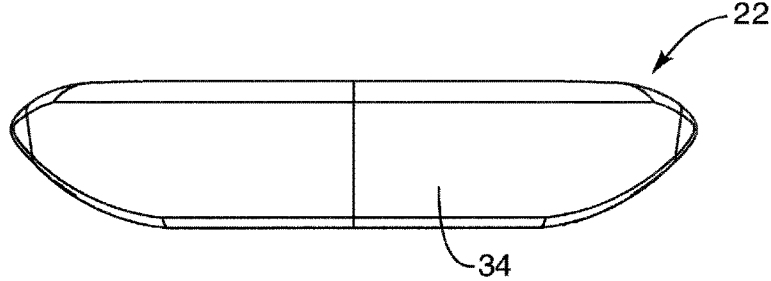
FIG. 11

DENTAL APPLIANCE FOR TREATMENT OF BRUXISM

RELATED APPLICATIONS

This application claims the benefit of U.S. Provisional Patent Application Ser. No. 61/841,682 filed Jul. 1, 2013 and U.S. Provisional Patent Application Ser. No. 61/901,696 filed Nov. 8, 2013, both of which are hereby incorporated by reference.

BACKGROUND

The Field of the Invention

This invention relates to dentistry and, more particularly, to novel systems and methods for treating bruxism.

The Background Art

Bruxism, or grinding and clenching of teeth, can cause irreversible damage to teeth and the temporomandibular joint (TMJ). For example, bruxism may contribute to a temporomandibular disorder (TMD). Accordingly, what is needed is an apparatus and method for preventing bruxism or the negative consequences thereof.

BRIEF SUMMARY OF THE INVENTION

In view of the foregoing, in accordance with the invention as embodied and broadly described herein, a method and apparatus are disclosed in one embodiment of the present invention as including a dental appliance for treating bruxism or symptoms associated therewith. In selected embodiments, the dental appliance may comprising an upper portion corresponding to one or more upper or maxillary teeth of a patient and a lower portion corresponding to one or more lower or mandibular teeth of the patient. The upper and lower portions may each include a base and a feature. Each base may be shaped to selectively engage one or more teeth of a patient. Each feature may be secured to a corresponding base. Thus, each base may interface between a corresponding feature and certain teeth of a patient. The upper and lower portions may be worn simultaneously to control one or more mandibular loadings, motions, or the like.

In selected embodiments, features may be positioned and shaped to interface or interact with one another in a particular manner. For example, when an appliance is in place, opposing features may be located on or secured to anterior areas of the respective bases. The features may be shaped, sized, or positioned such that contact therebetween may be or comprise an initial, primary, or exclusive point of contact for forces of occlusion passing form mandibular teeth to maxillary teeth of the corresponding patient. As a result, an appliance may cause all or a large portion of the forces of occlusion to be directed to the front of the mouth or to the front teeth. Since the brain of a patient may not allow the muscles of mastication to produce the same force of occlusion when pressure is only on the front teeth, an appliance may prevent the patient from clenching or grinding teeth.

As features interact with one another, they may change a position of a lower jaw of a patient. For example, in certain embodiments, a first feature may comprise an indentation or recess and a second, opposite feature may comprising a protrusion or recess. When directly contacting and opposing one another, the opposing features may maintain a certain initial separation between an upper and lower jaw. However, during a lateral excursion, a protrusion may pass or move out of alignment with an opposing indentation and begin to "climb" the walls of the indentation. Accordingly, in a laterally misaligned position, a new, greater separation between an upper and lower jaw may be applied or enforced. In certain embodiments or with certain patients, a greater separation in a lateral excursion may lower the strain imposed on the TMJ.

Alternatively, a first feature and a second, opposing feature may each comprise a protrusion. When directly contacting and opposing one another, such protrusions may maintain a certain initial separation between an upper and lower jaw. However, during a lateral excursion or the like, one protrusion may pass or move out of alignment with the other protrusion. Accordingly, in an misaligned position, a new, lower separation between an upper and lower jaw may be allowed or permitted. In certain embodiments or applications, or with certain patients, a lower separation may lower the strain imposed on the TMJ in a lateral excursion.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 8 is a first side view of the feature of FIG. 4;

FIG. 9 is a second, opposite side view of the feature of FIG. 4;

FIG. 10 is a rear view of the feature of FIG. 4;

FIG. 11 is a front view of the feature of FIG. 4;

DETAILED DESCRIPTION OF SELECTED EMBODIMENTS

Figure 1:
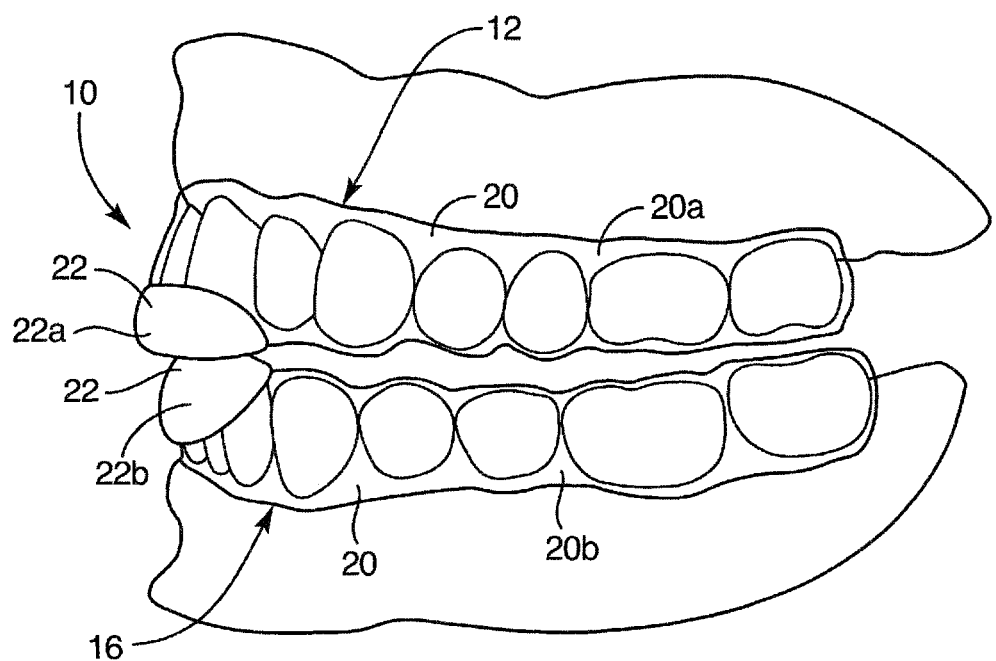
FIG. 1 is a side view of one embodiment of a dental appliance in accordance with the present invention installed on a patient.
Figure 1:
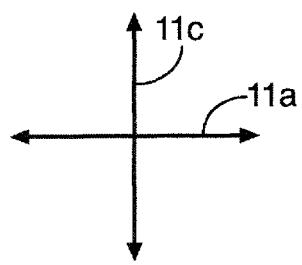

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Figure 2:
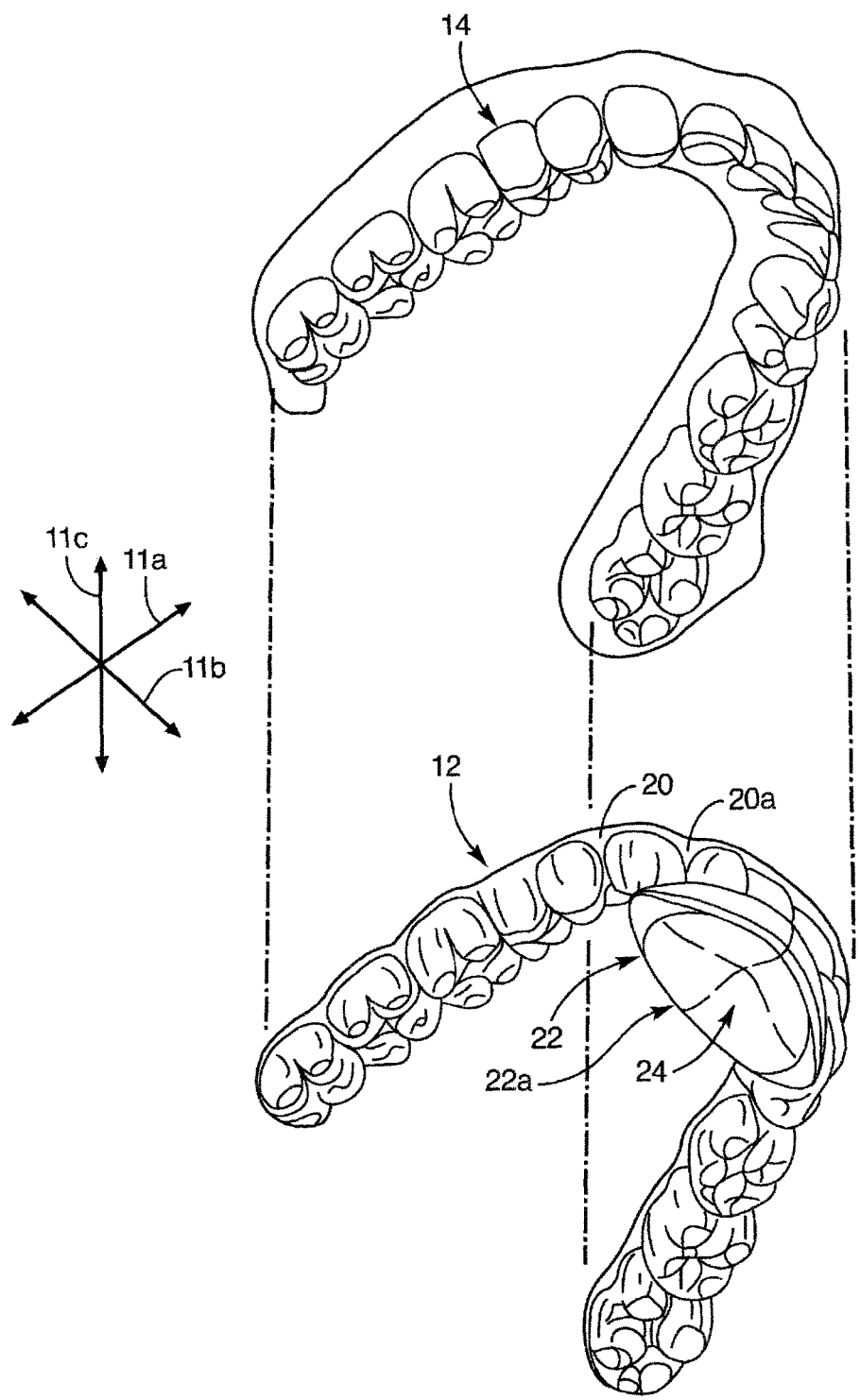
FIG. 2 is a perspective view of one embodiment of an upper portion of a dental appliance in accordance with the present invention.
Figure 3:
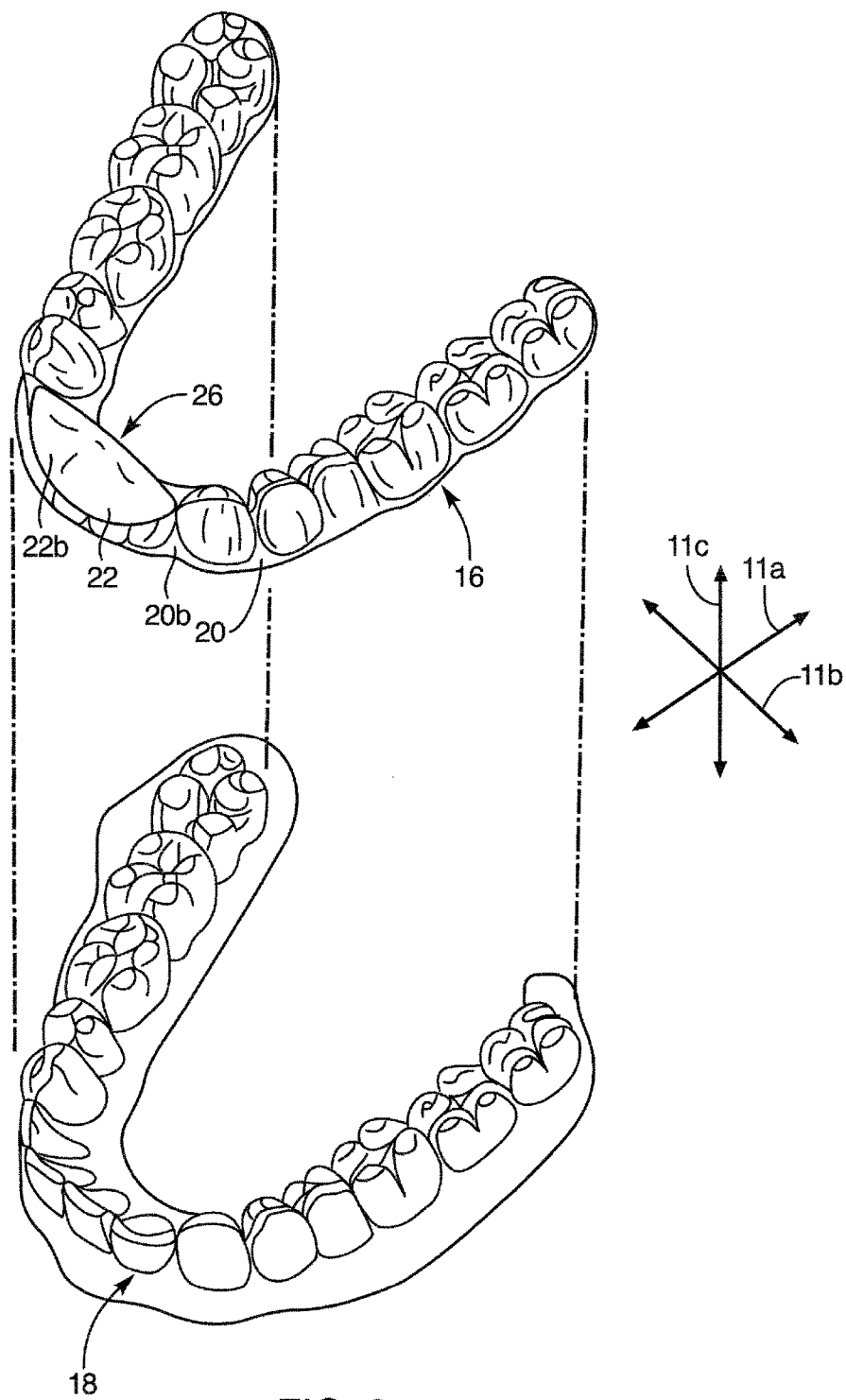
FIG. 3 is a perspective view of one embodiment of a lower portion of a dental appliance in accordance with the present invention.
Figure 4:
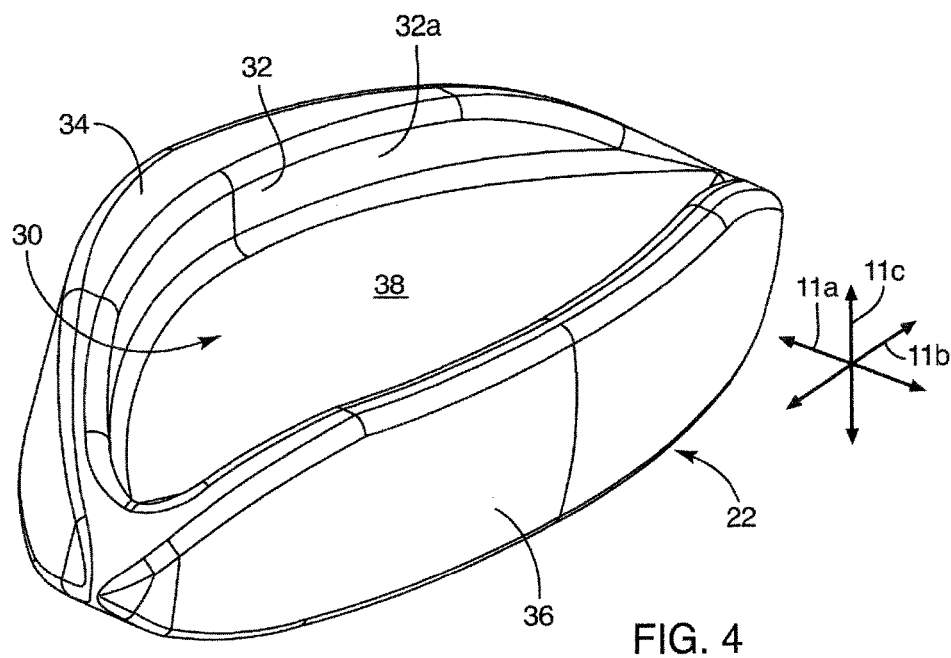
FIG. 4 is a perspective view of one embodiment of a feature having an indentation or recess in accordance with the present invention.

Referring to FIGS. 1-3, bruxism may cause unnecessary muscle strain, tension, and pain. For example, while grinding and clenching teeth, jaw muscles may be contracted and strained for extended periods of time. Additionally, grinding and clenching of teeth may cause muscle strain and tension in other areas. For example, bruxism may produce muscle strain, tension, and pain in the muscles of the neck. Bruxism may cause sleep problems as well.

For example, when the muscular systems of the head and neck are contracting, a patient may not enter deeper levels of sleep. Thus, habitual clenching and grinding can prevent the parasympathetic system from operating at its potential. A depressed immune system, lower metabolism, depressed neurotransmitter activity, lower reaction time, high stress levels, feelings of depression and more have all been documented and linked to lack of deep sleep.

Additionally, muscle tension and stress from over worked muscles and lack of sleep are a leading cause of headaches. When the brain receives too much bad sensory information, it may translate to a headache. The motor component of the trigeminal nerve can send a lot of bad sensory information to the brain. Thus, headaches may be a symptom of bruxism.

By treating bruxism, an appliance 10 in accordance with the present invention may cure a host of ailments. For example, an appliance 10 may protect teeth from harmful abrasion and unnecessary wear. An appliance 10 may also reduce inflammation of the periodontal ligament (PDL), reduce pulpitis of the teeth, preserve an orthodontic tooth position, reduce muscle strain, tension, and pain in the muscles of the jaw, reduce muscle strain, tension, and pain in the muscles of the neck, enable a user to enter deeper levels of sleep, and/or reduce head aches.

In describing an appliance 10 in accordance with the present invention, it may be helpful to define a coordinate system. For example, in selected embodiments, an appliance 10 may be described in terms of a longitudinal direction 11$a$, lateral direction 11$b$, and transverse direction 11$c$. The longitudinal, lateral, and transverse directions 11$a$, 11$b$, 11$c$ may extend orthogonally with respect to one another.

In selected embodiments, an appliance 10 in accordance with the present invention may include an upper portion 12 corresponding to (e.g., engaging, covering, being worn over) one or more upper or maxillary teeth 14 of a patient and a lower portion 16 corresponding to (e.g., engaging, covering, being worn over) one or more lower or mandibular teeth 18 of the patient. In certain embodiments, the upper and lower portions 12, 16 of an appliance 10 may be worn simultaneously.

An appliance 10 may cover all of the teeth of a patient or some subset thereof. For example, in selected embodiments, an upper portion 12 may engage or cover all or substantially all maxillary teeth 14 of a patient and a lower portion 16 may engage or cover all or substantially all mandibular teeth 18 of the patient. This may allow for orthodontic retention, product delivery (e.g., application of a whitening product to the teeth), or the like or a combination thereof. Alternatively, one or both of an upper portion 12 and a lower portion 16 may respectively cover less than (e.g., substantially less than) all of the maxillary and mandibular teeth of a patient.

In selected embodiments, upper and lower portions 12, 16 in accordance with the present invention may each include a base 20 and a feature 22. For example, an upper portion 12 may include a first base 20$a$ and a first feature 22$a$, while a lower portion 16 may include a second base 20$b$ and a second feature 22$b$.

A base 20 may be shaped to selectively engage one or more teeth of a patient. A feature 22 may be secured to a base 20. Thus, a base 20 may interface between a feature 22 and certain teeth of a patient. For example, a base 20 may be custom made to closely fit certain teeth of a patient. Accordingly, when the base 20 is applied to the one or more teeth, the base 20 may tend to stay there by mechanical gripping, suction, or the like or some combination thereof. Thus, once a base 20 is applied to one or more teeth, a corresponding feature 20 may be held in a desired orientation or position with respect to the teeth. However, the base 20 and corresponding feature 22 may be removed from the patient by simply pulling the base 20 away from the corresponding teeth.

In certain embodiments, an appliance 10 may include features 22 positioned opposite one another. For example, a first feature 22a of an upper portion 12 may be positioned opposite a second feature 22b of a lower portion 16. Accordingly, mandibular motion of a patient (e.g., biting down) may result in a first feature 22a contacting a second feature 22b.

In selected embodiments, features 22 may be positioned and shaped to interface or interact with one another in a particular manner. For example, a first feature 22a may comprise an indentation 24 or recess 24 and a second feature 22b may comprise a protrusion 26 or mound 26. Alternatively, a first feature 22a may comprise a protrusion 26 or mound 24 and a second feature 22b may comprise an indentation 24 or recess 24. Thus, while FIGS. 1-3 show an indentation 24 forming part of an upper portion 12 and a protrusion 26 forming part of a lower portion 16, in other embodiments, a protrusion 26 may form part of an upper portion 12 and an indentation 24 may form part of a lower portion 16.

In certain embodiments, features 22 may be positioned and shaped to interface or interact with one another to control, direct, or influence the mandibular motion, mandibular loadings, or the like of a corresponding patient. For example, when an appliance 10 is in place, opposing first and second features 22a, 22b may be located on or secured to anterior areas of the respective first and second bases 20a, 20b. Moreover, the first and second features 22a, 22b may be shaped, sized, or position such that contact therebetween may be or comprise an initial, primary, or exclusive point of contact for forces of occlusion (e.g., biting loads) or the like passing form mandibular teeth to maxillary teeth of the corresponding patient.

As a result, an appliance 10 may cause all forces of occlusion to be directed to the front of the mouth or to the front teeth (e.g., maxillary central incisors, maxillary lateral incisors, mandibular central incisors, mandibular lateral incisors, or the like or combinations or sub-combinations thereof). The brain of a patient may not allow the muscles of mastication to produce the same force of occlusion when pressure is only on the front teeth. That is, an appliance 10 may not allow the muscles around the joint to contract at full strength. Thus, an appliance may 10 may prevent a patient from clenching or grinding teeth and provide to the patient the benefits associated therewith.

An appliance 10 in accordance with the present invention may be manufactured in any suitable manner. In selected embodiments, a base 20 and corresponding feature 22 may be made as a monolithic unit by three-dimensional printing, photo-activation, machining, casting, molding, or the like. Alternatively, impressions (e.g., actual or digital impressions) of a patient's teeth may be taken and models of the patient's teeth may be fabricated. Polymeric material (e.g., acrylic sheets) may be applied to and/or formed around the modeled teeth to form first and second bases 20a, 20b. Thus, the bases 20 may be custom made to closely fit selected teeth of a patient. Once the bases 20 are formed, appropriate features 22 may be applied thereto.

Features 22 in accordance with the present invention may be manufactured from any suitable material or combinations of materials. Suitable materials may include polymers, ceramics, metals, metal alloys, or the like. In certain embodiments, features 22 be manufactured as separate, standardized pieces. That is, while a base 20 may be custom made to fit only one patient, a feature 22 may be an "off-the-shelf" item that may be applied to various bases 20. For example, features 22 may be manufactured in one size or in a relative small set of sizes (e.g., small, medium, large, etc.). Then, once a base 20 has been made, an appropriate feature 22 may be selected, positioned, and bonded to an anterior area of the base 20. Alternatively, a feature 22 may be formed by hand from a polymeric material, epoxy, or the like that is molten, in a softened condition, uncured, or the like and urged against or otherwise bonded to a base 20.

In selected embodiments, a feature 22a corresponding to an upper portion 12 may be positioned differently than a feature 22b corresponding to a lower portion 16. This difference may ensure that the two features 22a, 22b properly align when a lower jaw of the corresponding patient is in a desired position (e.g., a neutral, central, forward, lower, or mouth-slightly-open position, or a combination or sub-combination thereof). This desired position may be selected to control jaw position and postural muscles of the neck and head to open the airway of the patient, thereby decreasing snoring and reducing the incidence or symptoms of sleep apnea. For example, in certain embodiments, a feature 22a corresponding to an upper portion 12 may be positioned primarily or largely posterior and/or inferior to the maxillary central incisors, while a feature 22b corresponding to a lower portion 16 may be positioned primarily or largely superior (and possible anterior or posterior to) the mandibular central incisors.

Figure 5:
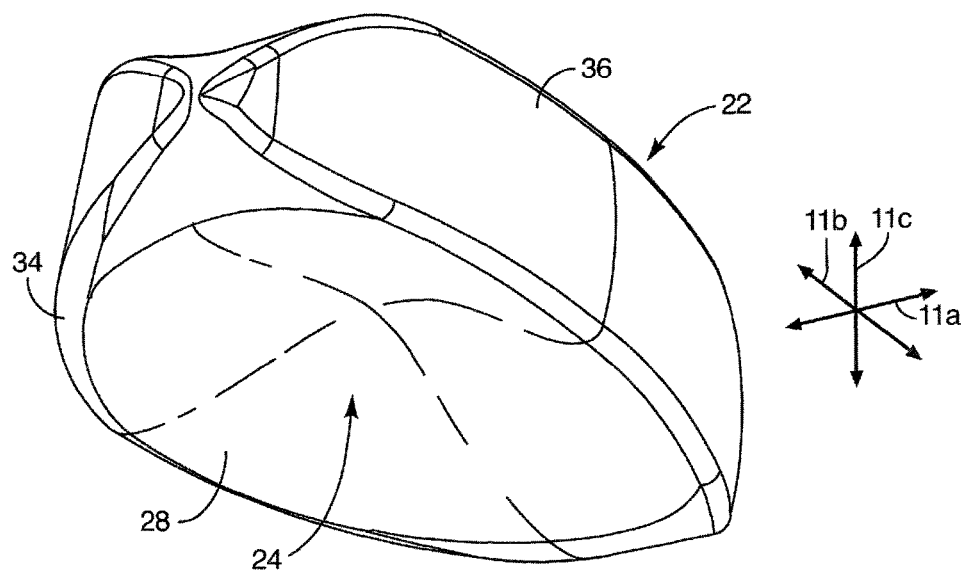
FIG. 5 is another perspective view of the feature of FIG. 4.
Figure 6:
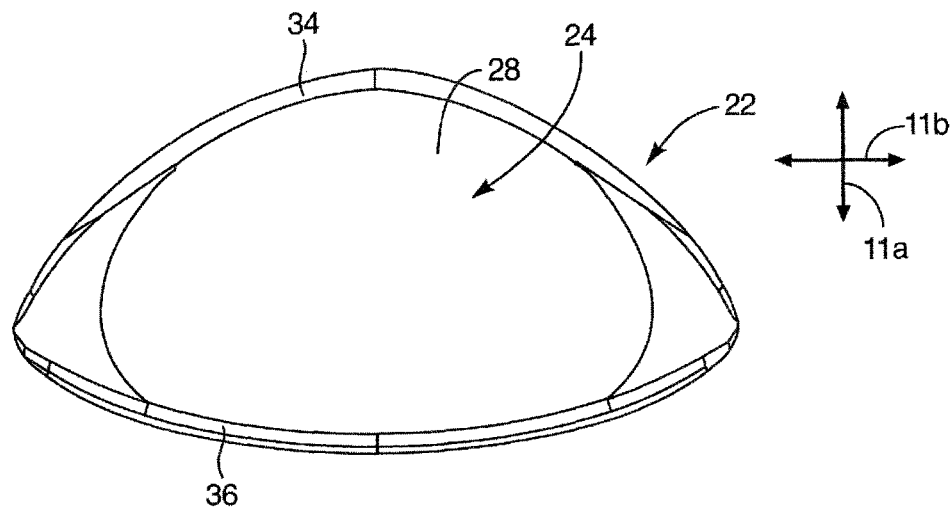
FIG. 6 is a bottom view of the feature of FIG. 4.
Figure 7:
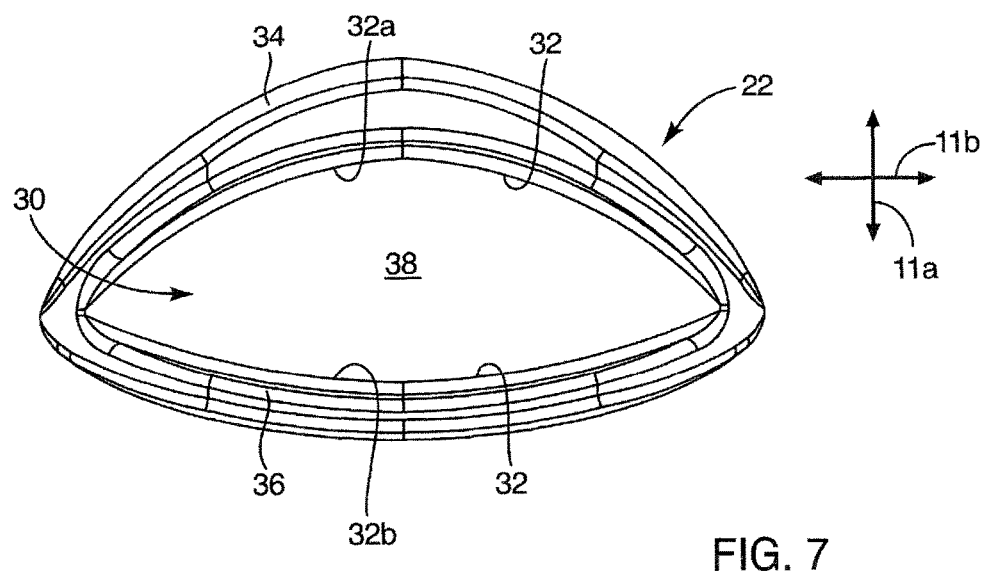
FIG. 7 is a top view of the feature of FIG. 4.
Figure 12:
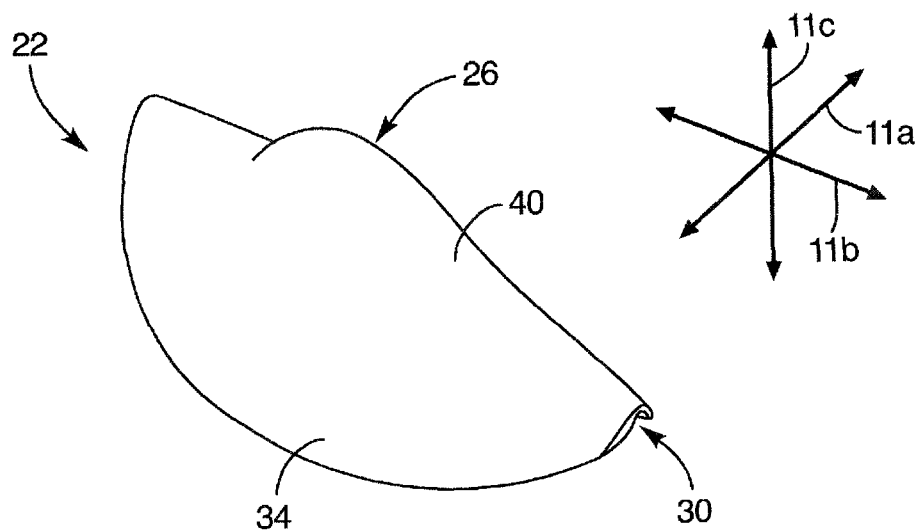
FIG. 12 is a perspective view of one embodiment of a feature having a protrusion or mound in accordance with the present invention.
Figure 13:
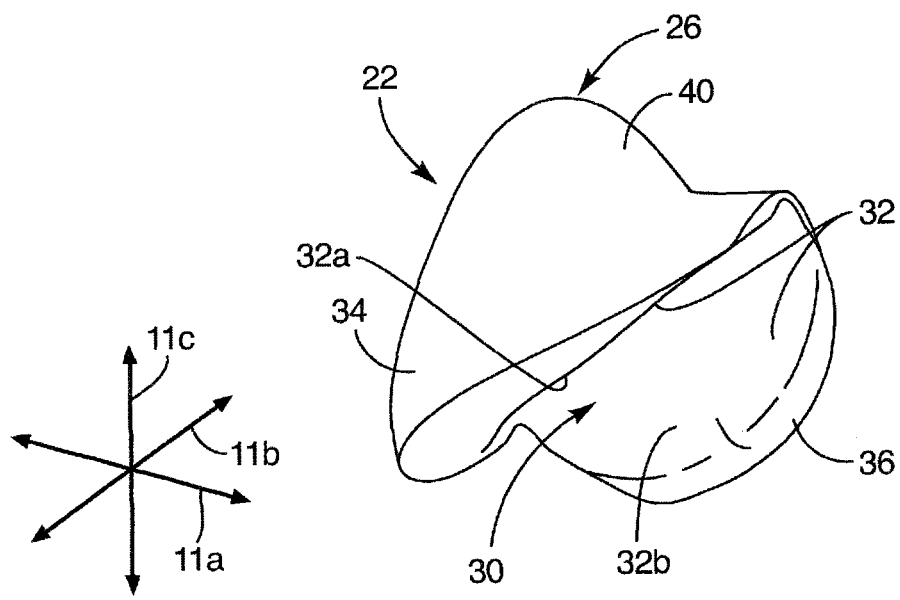
FIG. 13 is another perspective view of the feature of FIG. 12.
Figure 14:
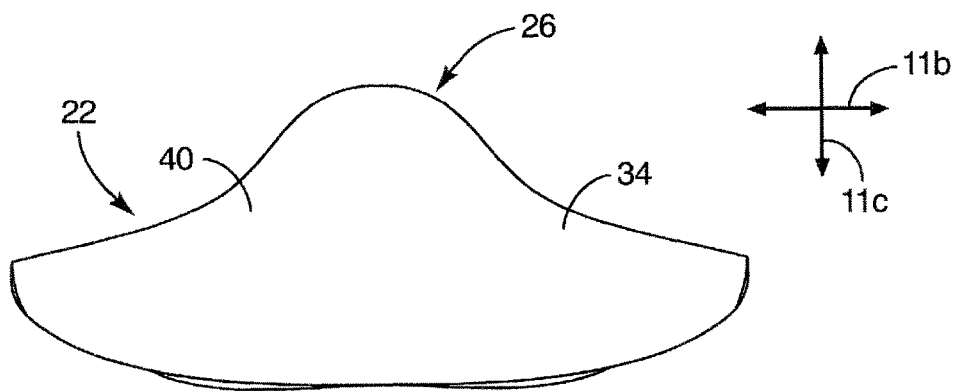
FIG. 14 is a front view of the feature of FIG. 12.
Figure 15:
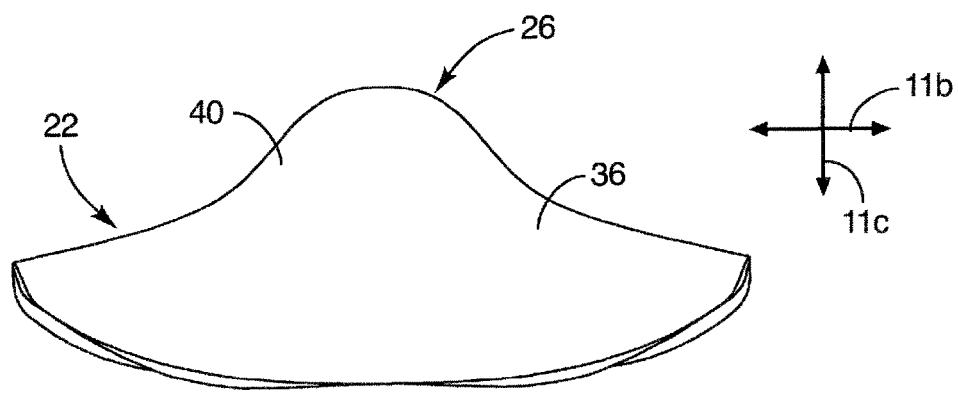
FIG. 15 is a back view of the feature of FIG. 12.
Figure 16:
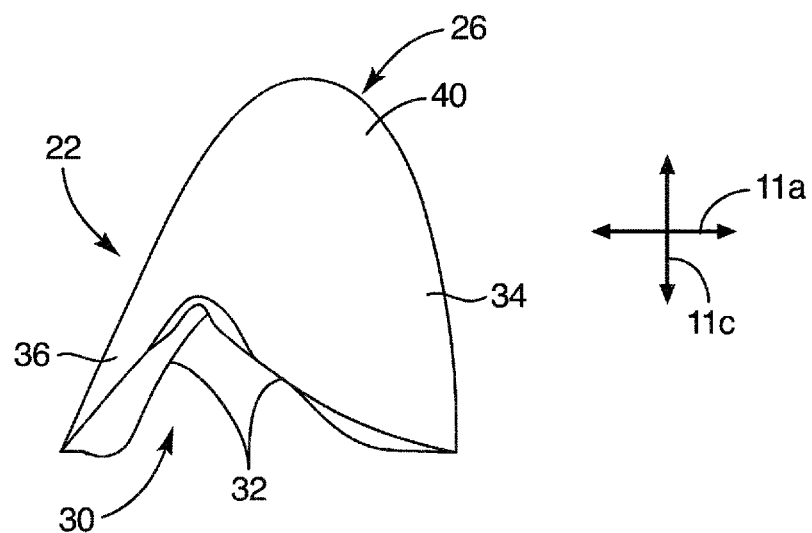
FIG. 16 is a first side view of the feature of FIG. 12.
Figure 17:
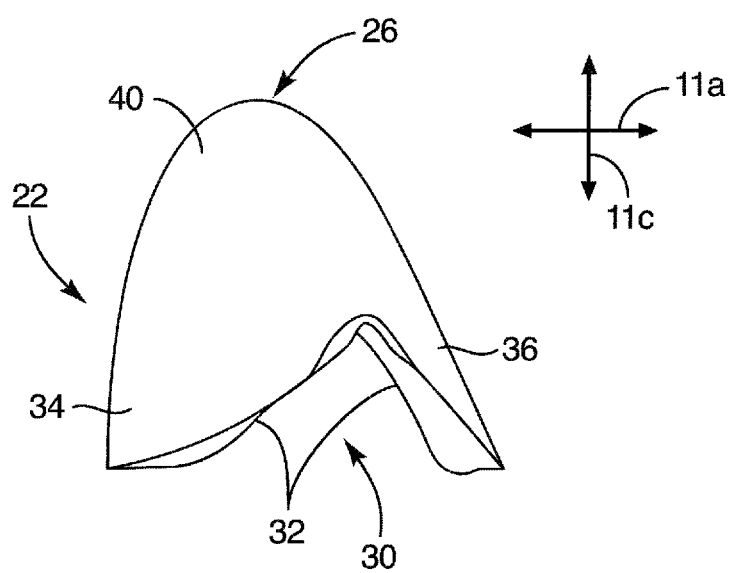
FIG. 17 is a second, opposite side view of the feature of FIG. 12.
Figure 18:
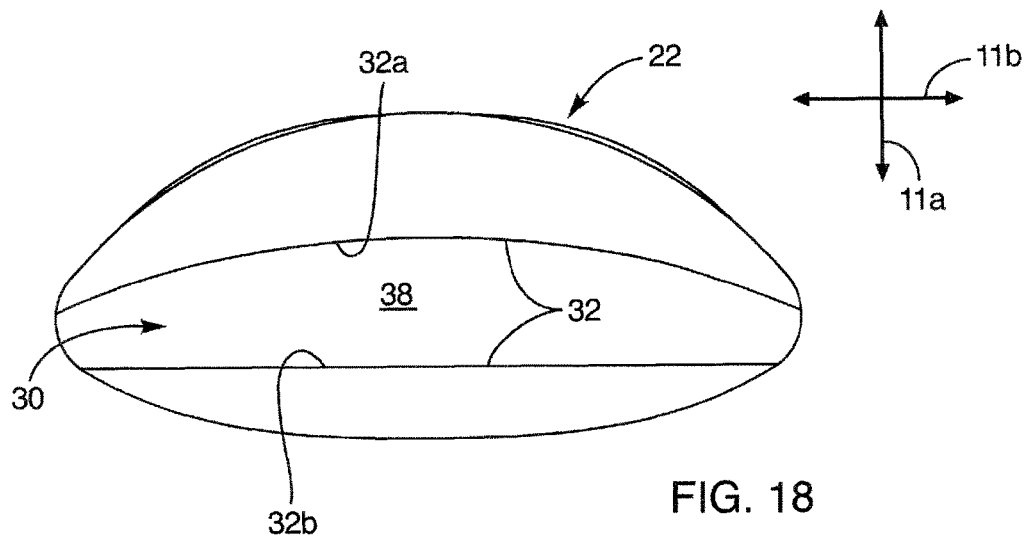
FIG. 18 is a bottom view of the feature of FIG. 12.
Figure 19:
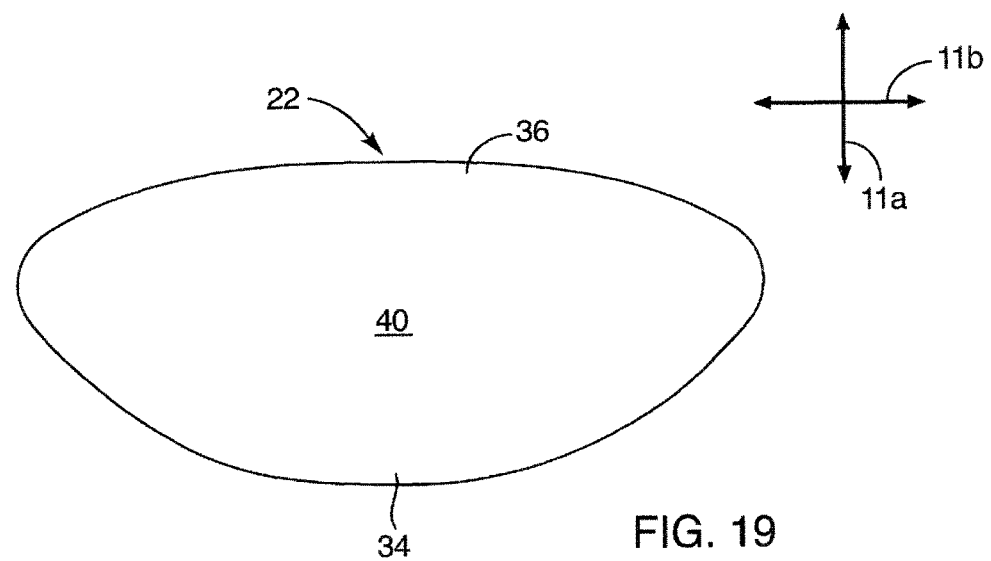
FIG. 19 is a top view of the feature of FIG. 12.
Figure 20:
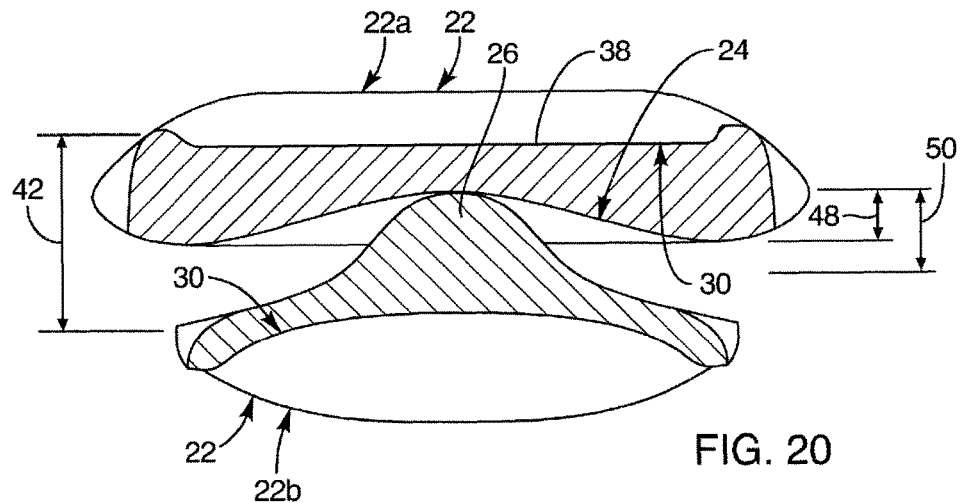
FIG. 20 is a partial, cross-sectional, front view of one embodiment of a dental appliance wherein the feature of FIG. 4 and the feature of FIG. 12 are abutting and aligned in accordance with the present invention.
Figure 21:
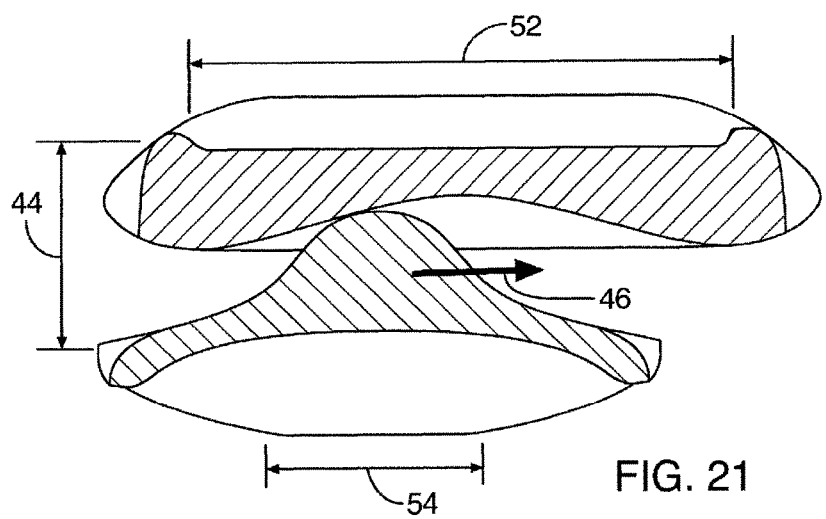
FIG. 21 is a partial, cross-sectional, front view the dental appliance of FIG. 20 wherein the feature of FIG. 4 and the feature of FIG. 12 are abutting and the feature of FIG. 12 is shifted to the left in accordance with the present invention.
Figure 22:
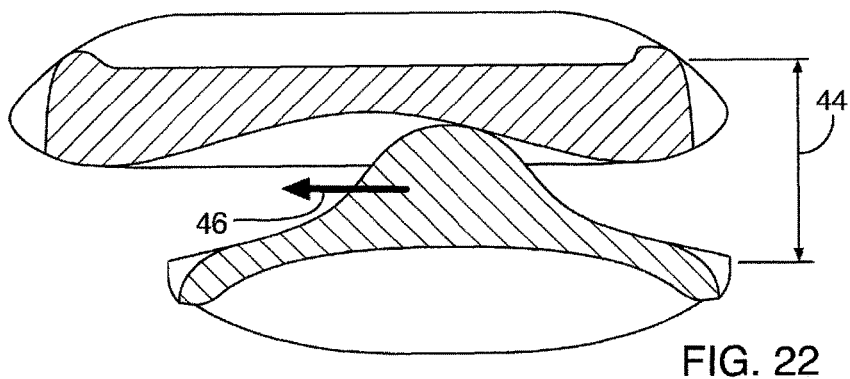
FIG. 22 is a partial, cross-sectional, front view the dental appliance of FIG. 20 wherein the feature of FIG. 4 and the feature of FIG. 12 are abutting and the feature of FIG. 12 is shifted to the right in accordance with the present invention.
Figure 23:
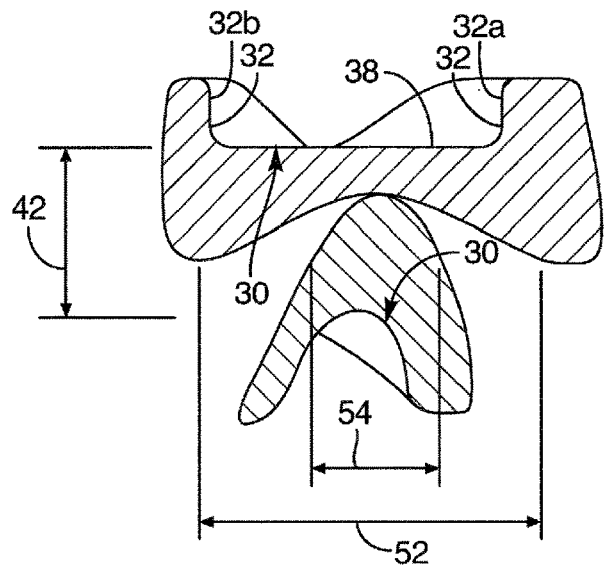
FIG. 23 is a partial, cross-sectional, side view on one embodiment of a dental appliance wherein the feature of FIG. 4 and the feature of FIG. 12 are abutting and aligned in accordance with the present invention.
Figure 24:
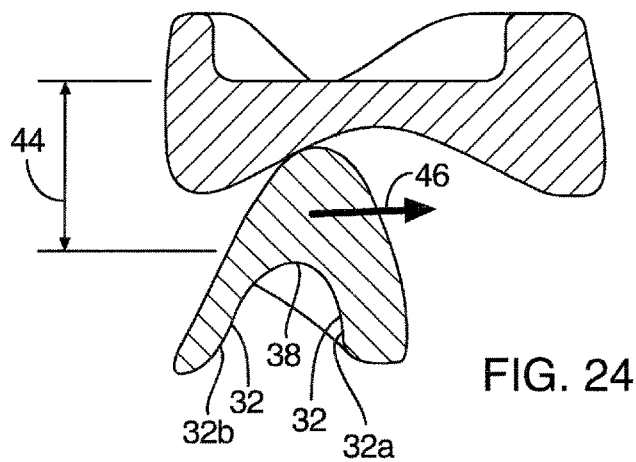
FIG. 24 is a partial, cross-sectional, side view the dental appliance of FIG. 23 wherein the feature of FIG. 4 and the feature of FIG. 12 are abutting and the feature of FIG. 12 is shifted rearward in accordance with the present invention.
Figure 25:
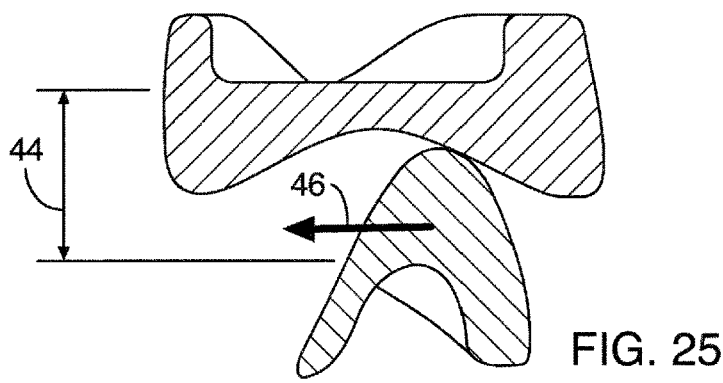
FIG. 25 is a partial, cross-sectional, side view the dental appliance of FIG. 23 wherein the feature of FIG. 4 and the feature of FIG. 12 are abutting and the feature of FIG. 12 is shifted forward in accordance with the present invention.
Figure 26:
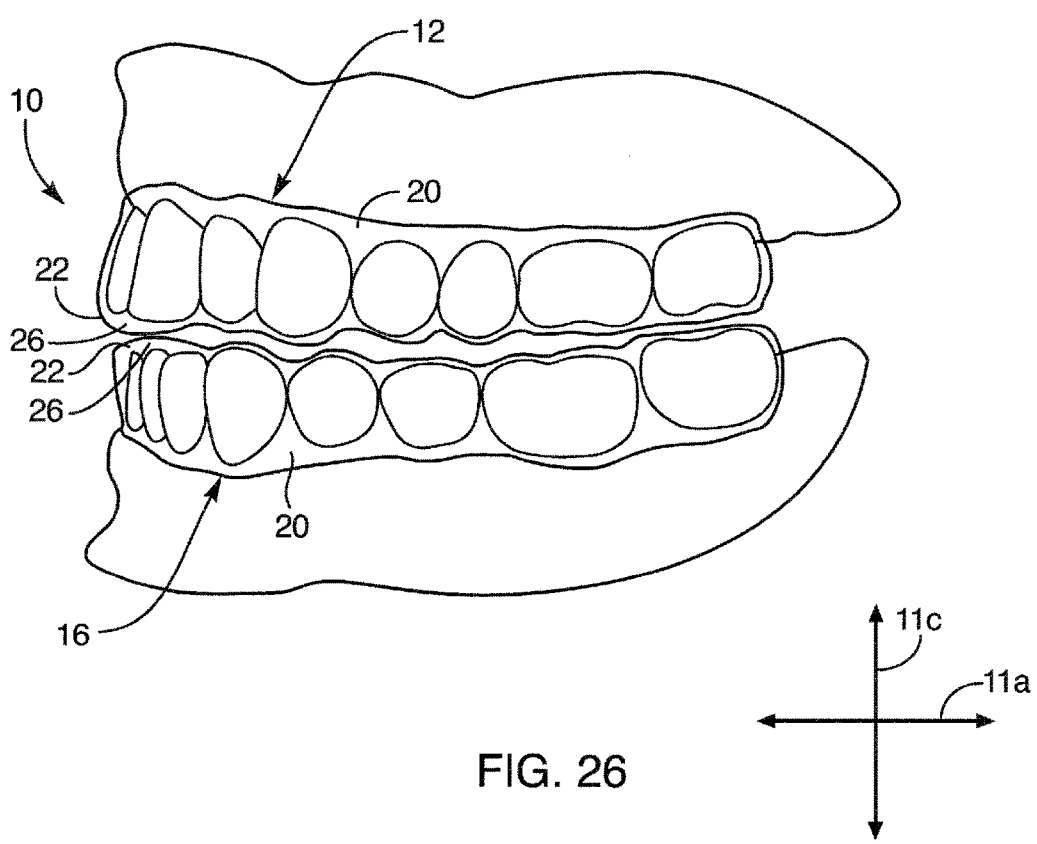
FIG. 26 is a side elevation view of an alternative embodiment of a dental appliance in accordance with the present invention installed on a patient.
Figure 27:
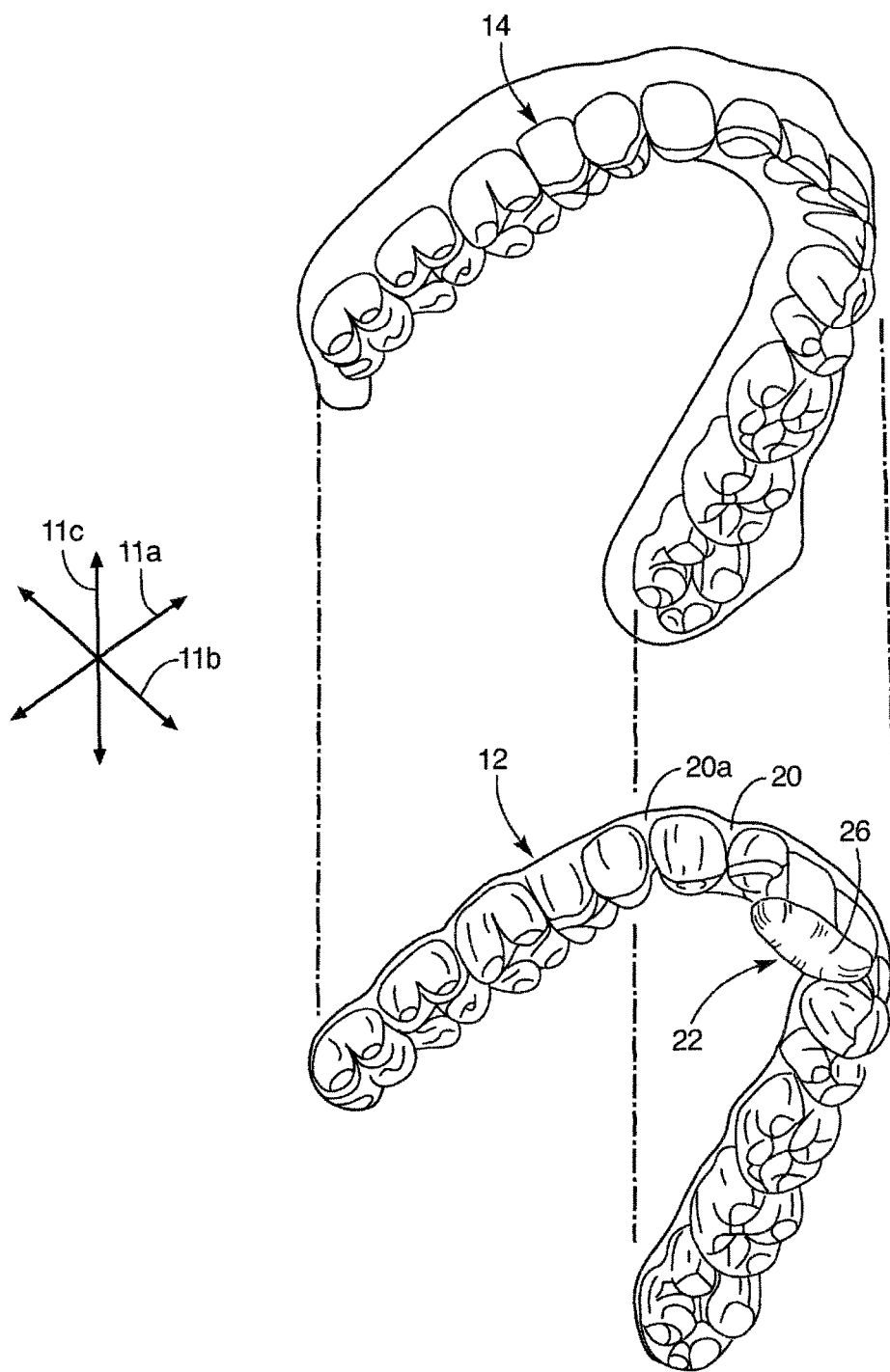
FIG. 27 is a perspective view of an alternative embodiment of an upper portion of a dental appliance in accordance with the present invention.
Figure 28:
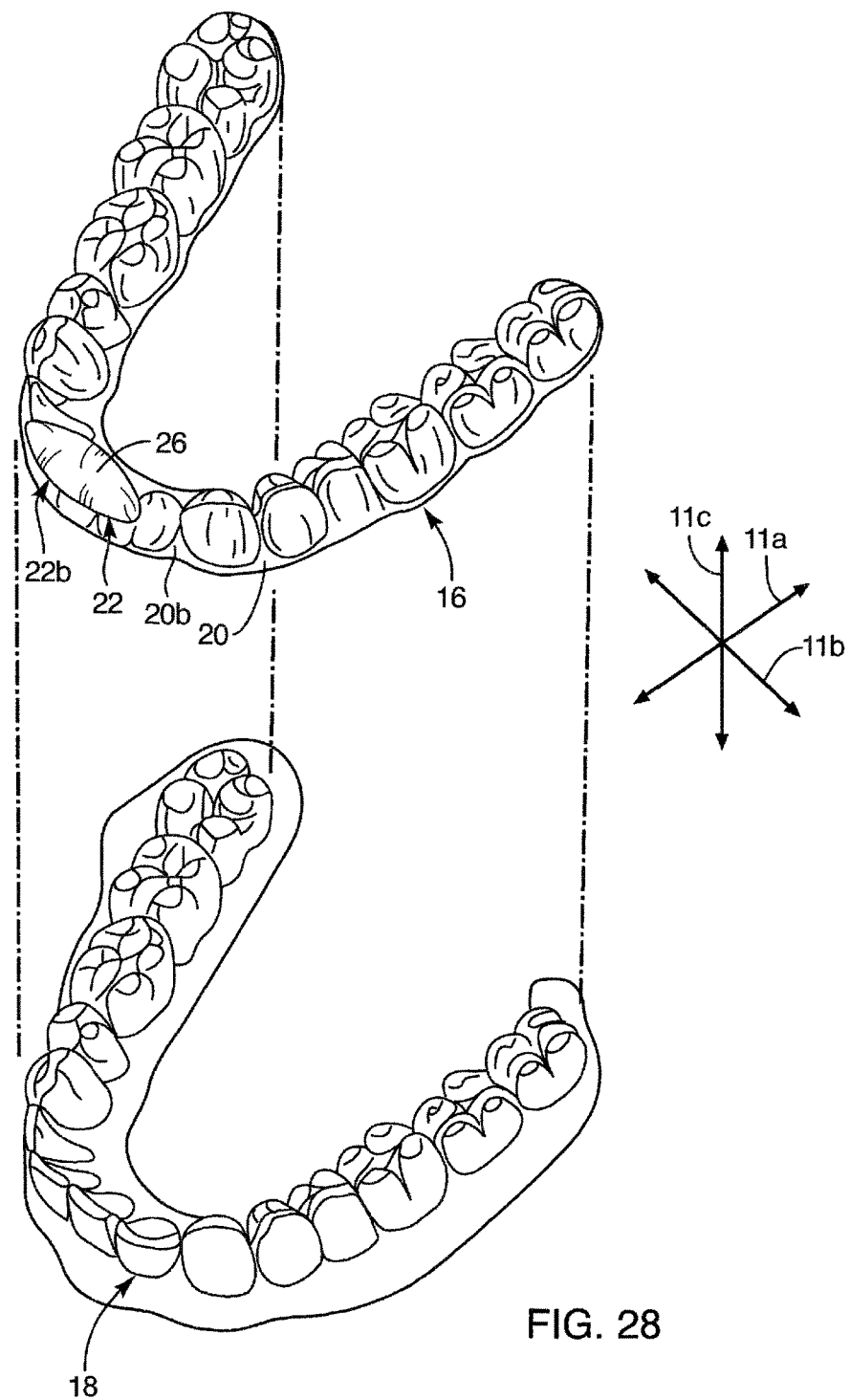
FIG. 28 is a perspective view of an alternative of a lower portion of a dental appliance in accordance with the present invention.
Figure 29:
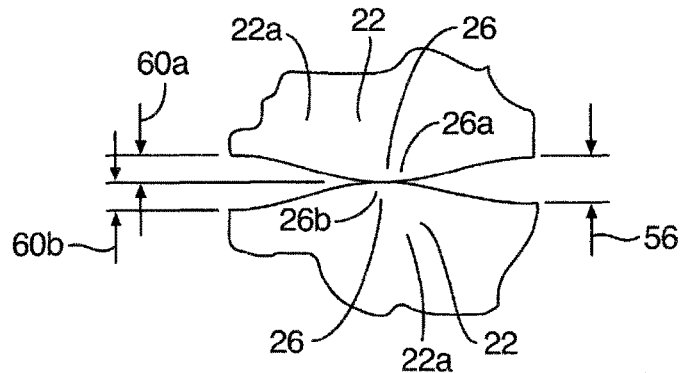
FIG. 29 is a partial front view of one embodiment of a dental appliance wherein opposing protrusions of the upper and lower portions are abutting and aligned in accordance with the present invention.
Figure 30:
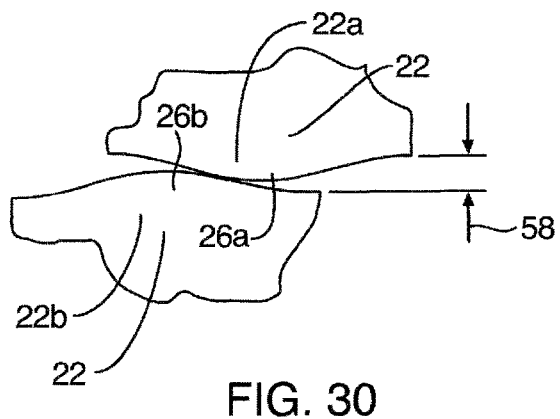
FIG. 30 is a partial front elevation view the dental appliance of FIG. 29 wherein the upper and lower portions are abutting and the lower portion is shifted to the left in accordance with the present invention.
Figure 31:
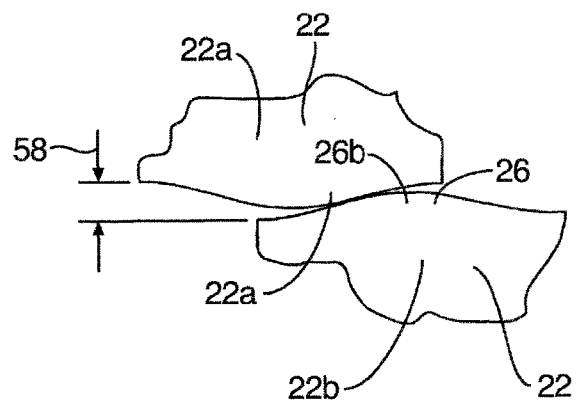
FIG. 31 is a partial front elevation view the dental appliance of FIG. 29 wherein the upper and lower portions are abutting and the lower portion is shifted to the right in accordance with the present invention.

Referring to FIGS. 4-11, a feature 22 providing or comprising an indentation 24 or recess 24 may have any suitable configuration. In selected embodiments, such a feature 22 may include a first side having a concave surface 28 forming a concavity, which concavity may be the indentation 24 or recess 24. As shown in FIG. 5, a concave surface 28 may have a deepest point and an outer boundary circumscribing the deepest point. The concave surface 28 may slope continuously from each point on the outer boundary to the deepest point. The feature 22 may also include a second side having a channel 30 facilitating securement of the feature 22 to a base 20.

For example, a channel 30 may provide a location for bonding material to be applied to a feature 22 before the feature 22 is applied to a corresponding base 20. Alternatively, or in addition thereto, in selected embodiments, an aperture 30 or channel 30 may include one or more curved surfaces 32 that track or loosely follow a typical curve associated with an anterior area of a base 20. That is, as a base 20 may curve to accommodate the natural positioning of the incisors, cuspids, bicuspids, etc. of the patient, so a channel 30 or curved surface 32 thereof may curve to accommodate the shape of the base 20. Accordingly, the curved surface 32 may facilitate positioning and stabilizing of a feature 22 with respect to a corresponding base 20.

In selected embodiments, a channel 30 may divide a feature 22 into an anterior portion 34 and a posterior portion 36. When connected to a base 20 and applied to a patient, an anterior portion 34 may be largely or exclusively position anterior to the teeth (e.g., incisors, cuspids, etc.) of the patient. Conversely, a posterior portion 36 may be positioned largely or exclusively posterior to those teeth.

In selected embodiments, one curved surface 32a or side of a channel 30 may be part of an anterior portion 34, while another, opposite curved surface 32b or side of the channel 30 may be part of a posterior portion 36. A channel 30 may have any suitable width in the longitudinal direction 11a between such opposing surfaces 32a, 32b. In selected embodiments, a channel 30 may have a width just wide enough to accommodate the outer or exposed portions of the incisors (or the incisors and cuspids) and the thickness of the base 20 extending thereover. Alternatively, a channel 30 may have a width that significantly wider than the teeth corresponding thereto.

For example, a channel 30 may have one curved surface 32a that tracks or loosely follows the curvature of the anterior side of the teeth, while an opposing curved surface 32b extends posteriorly away from a posterior side of the teeth. In such embodiments, the wide channel 30 may increase the stability with which the feature 22 may be secured to a base 20. Such stability may be helpful when a feature 22 comprises an indentation 24 or recess 24 positioned largely or entirely posterior to the corresponding teeth.

In selected embodiments, the width in the longitudinal direction 11a between opposing surfaces 32 of a channel 30 may be substantially constant across a feature 22 in the lateral direction 11b. That is, the width of the channel 30 may be substantially constant from one end of the channel 30 to the other. Alternatively, the width may vary. For example, in certain embodiments, a channel 30 may have the smallest width at the lateral 11b extremes thereof. The channel 30 may be the widest at a middle portion thereof.

In certain embodiments, curvature of the opposing surfaces 32 of a channel 30 may be complementary or track one another. For example, if a curved surface 32a corresponding to an anterior portion 34 of a feature 22 is primarily concave, then an opposing curved surface 32b corresponding to a posterior portion 36 of the feature 22 may be primarily convex. Alternatively, curvature of the opposing surfaces 32 of a channel 30 may be substantially opposite. For example, if a curved surface 32a corresponding to an anterior portion 34 of a feature 22 is primarily concave, then an opposing curved surface 32b corresponding to a posterior portion 36 of the feature 22 may also be primarily concave and extend away from the other surface 32a.

A channel 30 in accordance with the present invention may have any suitable floor 38 or ceiling 38 connecting the opposing curved surfaces 32 or sides. For example, a floor 38 or ceiling 38 may be substantially flat. Alternatively, a floor 38 or ceiling 38 may be curved (e.g., smoothly curving and transitioning from one curved surface 32a to the opposing curved surface 32b). In selected embodiments, a feature 22 corresponding to an indentation 24 or recess 24 may have a channel 30 with a floor 38 or ceiling 38 that is substantially flat, while a feature 22 corresponding to a protrusion 26 or mound 26 may have a channel 30 with a floor 38 or ceiling 38 that is smoothly curved as it transitions from one curved surface 32a to the opposing curved surface 32b.

The various edges and surfaces of a feature 22 may be radiused and smooth. Smooth, radiused edges and smooth surfaces may enhance the comfort experienced by a patient in wearing an appliance 10 in accordance with the present invention. For example, an upper lip of a patient may rest on an anterior portion 34 of a feature 22 of an upper portion 12 of an appliance 10. Accordingly, the anterior portion 34 may be radiused and smooth to avoid irritating or harming the tender tissues on the interior of the upper lip. Similarly, the tip of a tongue of a patient may rest on a posterior portion 36 of a feature 22 of an upper portion 12 of an appliance 10. Accordingly, the posterior portion 34 may be radiused and smooth to avoid irritating or harming the tongue of the patient.

Referring to FIGS. 12-19, a feature 22 providing or comprising a protrusion 26 or mound 26 may have any suitable configuration. In selected embodiments, such a feature 22 may include a first side having a convex surface 40 forming the protrusion 26 or mound 26. The feature 22 may also include a second side having an aperture 30 or channel 30 facilitating securement of the feature 22 to a base 20. In certain embodiments, such an aperture 30 or channel 30 may include one or more curved surfaces 32 that track or loosely follow a typically curve associated with an anterior area of a base 20.

Referring to FIGS. 20-25, in selected embodiments, as features 22 interact with one another, they may change a position of a lower jaw of a patient. For example, when lateral excursions (e.g., when a lower jaw moves side to side in the lateral direction 11b) take place, opposing features 22 may lessen the strain in the TMJ. That is, when directly contacting and opposing one another, the opposing features 22 may maintain a certain initial separation 42 between an upper and lower jaw. However, during a lateral excursion, a protrusion 26 may pass or move out of alignment with an opposing indentation 26. That is, a protrusion 26 may move along and "climb" the walls of an indentation 24. In a laterally misaligned position, a new, greater separation 44 between an upper and lower jaw may be applied or enforced. In certain embodiments or with certain patients, this greater separation 44 in a lateral excursion may lower the strain imposed on the TMJ.

Similarly, in certain embodiments during a longitudinal excursion (e.g., when a lower jaw moves in or out in the longitudinal direction 11a), a protrusion 26 may pass or move out of alignment with an opposing indentation 24. As with a lateral excursion, a longitudinal excursion may cause a protrusion 26 may move along and "climb" the walls of an indentation 24. Accordingly, in a longitudinally misaligned position, a new, greater separation 44 between an upper and lower jaw may also be applied or enforced.

Alternatively, one or both features 22 may be formed such that longitudinal excursions produce no significant change in the initial separation 42 between an upper and lower jaw. For example, an indentation 24 may form a channel extending longitudinally 11a through an corresponding feature 22. Thus, a lateral excursion may cause a protrusion 26 to contact and climb the sides of the channel to produce a greater spacing 44, while a longitudinal excursion may permit the protrusion 22 to simply slide along the channel without changing the initial spacing 42.

A protrusion 26 and indentation 24 in accordance with the present invention may have any suitable fit or relative size therebetween. For example, in selected embodiments, a protrusion 26 may be significantly thinner than an opposing indentation 24 in the longitudinal direction 11a, the lateral direction 11b, or both the longitudinal and lateral directions 11a, 11b. In such embodiments, a protrusion 26 may move within an opposing indentation 24 through a sizable range of motion in the longitudinal direction 11a, the lateral direction 11b, or both the longitudinal and lateral directions 11a, 11b, respectively.

Alternatively, a protrusion 26 may be closer to the size of an opposing indentation 24 in the longitudinal direction 11a, the lateral direction 11b, or both the longitudinal and lateral directions 11a, 11b. In such embodiments, a protrusion 26 may move within the indentation 24 through a smaller range of motion in the longitudinal direction 11a, the lateral direction 11b, or both the longitudinal and lateral directions 11a, 11b, respectively. In certain embodiments, a protrusion 26 may substantially match the size of an opposing indentation 24 in one or both of the longitudinal and lateral directions 11a, 11b. Thus, longitudinal and/or lateral excursions may only be permitted to the extent that the protrusion 26 exits the opposing indentation 24.

Accordingly, the relative sizing and shapes of a protrusion 26 and opposing indentation 24 may define to a certain degree the range of motion of a lower jaw with respect to an upper jaw. Additionally, in selected embodiments, the relative sizing and shapes of a protrusion 26 and opposing indentation 24 may define or generate a biasing force urging a lower jaw into a particular alignment (e.g., a neutral and/or centered alignment) with an upper jaw. For example, the sides of an indentation 24 may bias an opposing protrusion 26 toward a center of the indentation 24. That is, if a protrusion 22 is contacting the sides of an indentations 20 as shown in FIGS. 21, 22, 24, 25, forces of occlusion may result in a centering force 46 urging a lower jaw to return to a desired (e.g., a neutral and/or centered) alignment.

In selected embodiments, each feature 22 and the surfaces 28, 40 thereof may extend gradually and smoothly from the surrounding area of the respective portions 12, 16. Accordingly, in such embodiments, when in contact with one another, opposing features 22 may move smoothly over one another (e.g., in lateral excursions, longitudinal excursions, or both lateral and longitudinal excursions).

Indentations 24 and protrusions 26 in accordance with the present invention may have any suitable depth 48 and height 50, respectively. In selected embodiments, the depth 48 of a particular indentation 24 may be less than or substantially equal to the height 50 of a corresponding protrusion 26. In certain embodiments, the height 50 of a protrusion 26 may be in a range from about 1 mm to about 12 mm and preferably from about 3 mm to about 8 mm. In such embodiments, the depth 48 of an indentation 24 may also be in a range from about 1 mm to about 12 mm and preferably from about 3 mm to about 8 mm.

Similarly, indentations 24 and protrusions 26 in accordance with the present invention may have any suitable base widths 52, 54, respectively. In selected embodiments, the base width 52 of a particular indentation 24 in both the longitudinal and lateral directions 11a, 11b may be greater than or substantially equal to the base width 54 of a corresponding protrusion 26 in both the longitudinal and lateral directions 11a, 11b.

In certain embodiments, the base width 54 of a protrusion 26 in the lateral direction 11b may be in a range from about 2 mm to about 15 mm and preferably from about 5 mm to about 10 mm. In such embodiments, the base width 52 of an indentation 24 in the lateral direction 11b may be in a range from about 3 mm to about 30 mm and preferably from about 10 mm to about 20 mm.

In certain embodiments, the base width 54 of a protrusion 26 in the longitudinal direction 11a may be less than the base width 52 of an indentation 24 in the lateral direction 11b. For example, the base width 54 of a protrusion 26 in the longitudinal direction 11a may be in a range from about 2 mm to about 12 mm and preferably from about 5 mm to about 8 mm. In such embodiments, the base width 52 of an indentation 24 in the longitudinal direction may be in a range from about 3 mm to about 20 mm and preferably from about 8 mm to about 15 mm.

Referring to FIGS. 26-31, in certain alternative embodiments, an appliance 10 may include two opposing protrusions 26 or mounds 26, one on the anterior section of each portion 12, 16. When an appliance 10 is in place, opposing protrusions 26 on the anterior sections of the upper and lower portions 12, 16 may form an initial, primary, or exclusive point of contact between an upper jaw and a lower jaw. This may cause all forces of occlusion to be directed to the front of the mouth or to the front teeth and, therefore, prevent a patient from clenching or grinding teeth and provide to the patient the benefits associated therewith.

In selected embodiments, opposing protrusions 26 may change a position of a lower jaw. For example, when lateral excursions take place, opposing protrusions 26 may lessen the strain in the TMJ. That is, when directly contacting and opposing one another, two protrusions 26 may maintain a certain initial separation 56 between an upper and lower jaw. However, during a lateral excursion, one protrusion 26a may pass or move out of alignment with the other protrusion 26b. That is, one protrusion 26a may slide off of the other protrusion 26b. In an misaligned position, a new, lower separation 58 between an upper and lower jaw may be allowed or permitted. In certain embodiments or applications, or with certain patients, a lower separation 58 may lower the strain imposed on the TMJ in a lateral excursion.

In certain embodiments, during a longitudinal excursion, one protrusion 26a may pass or move out of alignment with the other protrusion 26b. In an misaligned position, a new, lower separation 58 between an upper and lower jaw may be allowed or permitted. Alternatively, one or both protrusions 26 may be formed such that longitudinal excursions produce no new or lower separation 58 between an upper and lower jaw.

In selected embodiments, each protrusion 26 may extend gradually and smoothly from the surrounding area of the respective portions 12, 16. Accordingly, in such embodiments, when in contact with one another, opposing protrusions 26 may move smoothly over one another (e.g., in lateral excursions, longitudinal excursions, or both lateral and longitudinal excursions).

Protrusions 26 in accordance with the present invention may have any suitable height 60. In selected embodiments, opposing protrusions 26a, 26b may have different heights 60a, 60b. Alternatively, the heights 60a, 60b of the opposing protrusions 26a, 26b may be equal. In certain embodiments, the height 60 of each protrusion 26 may be in a range from about 1 mm to about 6 mm and preferably from about 3 mm to about 6 mm. The width (e.g., base width) of each protrusion 26 may be in a range from about 5 mm to about 20 mm and preferably from about 10 mm to about 15 mm.

An appliance 10 with opposing protrusions 26 may be manufactured in any suitable manner. In selected embodiments, impressions of a patient's teeth may be taken, models of patient's teeth may be fabricated, and then polymeric material (e.g., acrylic sheets) may be applied to and/or formed around the modeled teeth to form appropriate bases 20. Protrusions 26 may then be positioned appropriately and bonded to the bases 20 on the anterior area thereof.

Bonding a protrusion 26 to a base 20 may be done by bonding on a feature 22 manufactured as separate, standardized piece. Alternatively, a feature 22 and corresponding protrusion 26 may be formed by hand from a polymeric material, epoxy, or the like that is molten, in a softened condition, uncured, or the like and urged against or otherwise bonded to a base 20.

In selected embodiments, a protrusion 26a corresponding to an upper portion 12 may be positioned differently than a protrusion 26b corresponding to a lower portion 16. This difference may ensure that the two protrusions 26a, 26b properly align when a lower jaw is in a desired position (e.g., a neutral position). For example, in certain embodiments, a protrusion 26a corresponding to an upper portion 12 may be positioned primarily behind the maxillary central incisors, while a protrusion 26b corresponding to a lower portion 16 may be positioned primarily over or just slightly behind the mandibular central incisors.

U.S. Pat. No. 6,666,212 issued Dec. 23, 2003 is hereby incorporated by reference.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method for relieving symptoms related to bruxism, the method comprising:
   selecting one particular, three-dimensional alignment of a lower jaw of a patient with respect to an upper jaw of the patient;
   obtaining a dental appliance comprising
      an upper portion comprising a first base and a first feature, the first base shaped to engage upper teeth of the patient, the first feature securing to an anterior area of the first base and comprising one of (1) a protrusion having a peak and (2) a concave surface having a deepest point and an outer boundary circumscribing the deepest point, the concave surface sloping continuously from each point on the outer boundary to the deepest point,
      a lower portion comprising a second base and a second feature, the second base shaped to engage lower teeth of the patient, the second feature securing to an anterior area of the first base and comprising the other of the protrusion and the concave surface, and
      the upper and lower portions, wherein the concave surface and the protrusion are respectively shaped, positioned, and oriented such that contact of the peak with the deepest point corresponds to the one particular alignment;
   applying the appliance to the patient so that the upper portion moves with the upper teeth and the lower portion moves with the lower teeth;
   generating, by the patient while biting down on the appliance, a biting force urging the protrusion directly against the concave surface;
   generating, by the appliance as a reaction to the biting force, a centering force urging a lower jaw of the patient toward the one particular alignment whenever the peak is not in contact with the deepest point.

2. The method of claim 1, wherein the first and second bases each comprise polymeric material that follows contours of at least selected teeth of the patient.

3. The method of claim 2, wherein the first and second features each comprise polymeric material.

4. The method of claim 3, wherein the first and second features are bonded to the first and second bases, respectively.

5. The method of claim 4, wherein the first base is positioned between the upper teeth and the first feature.

6. The method of claim 5, wherein the second base is positioned between the lower teeth and the second feature.

7. The method of claim 6, wherein:
   the first feature comprises the concave surface; and
   the second feature comprises the protrusion.

8. The method of claim 7, wherein the applying the appliance to the patient results in:
   a majority of the concave surface being positioned posterior to the maxillary central incisors of the patient; and
   a majority of the protrusion being positioned superior to the mandibular central incisors of the patient.

9. The method of claim 2, wherein the polymeric material corresponding to the first base follows contours of substantially all of the upper teeth of the patient.

10. The method of claim 2, wherein the polymeric material corresponding to the second base follows contours of substantially all of the lower teeth of the patient.

11. A method for relieving symptoms related to bruxism, the method comprising:
    selecting one particular, three-dimensional alignment of a lower jaw of a patient with respect to an upper jaw of the patient;
    obtaining a dental appliance comprising
       an upper portion having a first anterior feature comprising a concave surface having a deepest point and an outer boundary circumscribing the deepest point, the concave surface sloping continuously from each point on the outer boundary to the deepest point,
       a lower portion having a second anterior feature comprising a protrusion having a peak, and
       the upper and lower portions, wherein the concave surface and the protrusion are respectively shaped, positioned, and oriented such that contact of the peak with the deepest point corresponds to the one particular alignment;
    applying the appliance to a patient so that the upper portion moves with upper teeth of the patient and the lower portion moves with lower teeth of the patient;
    generating, by the patient as a result of biting down on the appliance, a biting force urging the protrusion directly against the concave surface; and
    generating, by the appliance as a reaction to the biting force, a centering force urging a lower jaw of the patient toward the one particular alignment whenever the peak is not in contact with the deepest point.

* * * * *